United States Patent
Deutsch

(10) Patent No.: US 9,283,490 B1
(45) Date of Patent: Mar. 15, 2016

(54) DEVICE FOR STABILISING A FLYING ATTITUDE OF A REMOTE-CONTROLLED FIXED-WING AIRCRAFT

(71) Applicant: Richard Deutsch, Donauwoerth (DE)

(72) Inventor: Richard Deutsch, Donauwoerth (DE)

(73) Assignee: POWERBOX-SYSTEMS GMBH, Donauwoerth (DE)

(*) Notice: Subject to any disclaimer, the term of this patent is extended or adjusted under 35 U.S.C. 154(b) by 148 days.

(21) Appl. No.: 14/017,952

(22) Filed: Sep. 4, 2013

(30) Foreign Application Priority Data

Jan. 30, 2013 (DE) .......................... 10 2013 201 554

(51) Int. Cl.
| | |
|---|---|
| G05D 1/12 | (2006.01) |
| A63H 27/00 | (2006.01) |
| A63H 27/26 | (2006.01) |
| G05D 1/08 | (2006.01) |
| G05D 1/02 | (2006.01) |

(52) U.S. Cl.
CPC ................ *A63H 27/02* (2013.01); *A63H 27/06* (2013.01); *G05D 1/0204* (2013.01); *G05D 1/0816* (2013.01); *B64C 2203/00* (2013.01)

(58) Field of Classification Search
CPC ............... G05D 1/0816; G05D 1/0204; B64C 2203/00; B64C 17/06; A63H 27/02; A63H 27/06
See application file for complete search history.

(56) References Cited

U.S. PATENT DOCUMENTS

| | | | | |
|---|---|---|---|---|
| 5,058,824 | A * | 10/1991 | Cycon et al. | 244/17.13 |
| 6,088,633 | A | 7/2000 | Yamamoto | |
| 6,227,482 | B1 | 5/2001 | Yamamoto | |
| 7,219,861 | B1 * | 5/2007 | Barr | 244/190 |
| 7,302,316 | B2 * | 11/2007 | Beard et al. | 701/11 |
| 8,473,117 | B1 * | 6/2013 | McConville | 701/2 |
| 8,674,813 | B2 * | 3/2014 | Alexander et al. | 340/12.1 |
| 8,874,282 | B2 * | 10/2014 | Fredriksson | 701/2 |
| 2004/0082269 | A1 * | 4/2004 | Wright | 446/456 |
| 2007/0118493 | A1 * | 5/2007 | Jaffe | 706/25 |
| 2009/0069956 | A1 * | 3/2009 | Taya et al. | 701/2 |
| 2009/0216391 | A1 | 8/2009 | Manfred et al. | |

FOREIGN PATENT DOCUMENTS

DE    10 2005 006 993 B4    9/2006

* cited by examiner

*Primary Examiner* — Philip J Bonzell
*Assistant Examiner* — Michael Kreiner
(74) *Attorney, Agent, or Firm* — Manabu Kanesaka

(57) ABSTRACT

The invention relates to a method for adjusting parameters in a stabilizing device (4) for stabilizing a flying attitude of a remote-controlled fixed-wing aircraft. To adjust a first parameter for a first axis, a first adjustment signal is transmitted from the transmitter (1) to the stabilizing device (4). The first parameter (P1) is stored during the flight as a result of a first memory signal transmitted from the transmitter (1). A second parameter (P2) for a second axis is then adjusted and stored in a similar manner.

Figure 1:
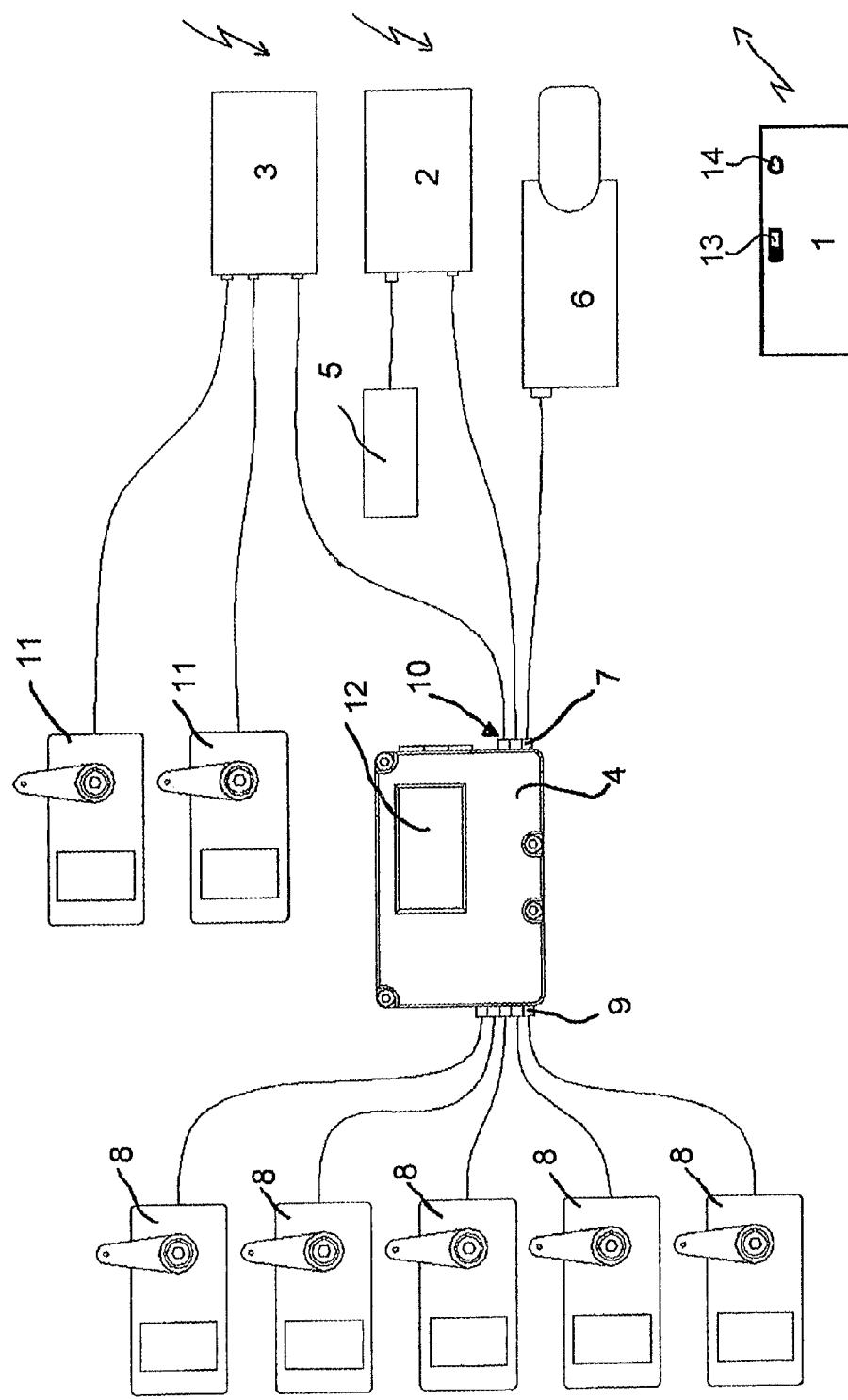

11 Claims, 3 Drawing Sheets

US 9,283,490 B1

DEVICE FOR STABILISING A FLYING ATTITUDE OF A REMOTE-CONTROLLED FIXED-WING AIRCRAFT

RELATED APPLICATIONS

The present application is based on, and claims priority from, German Application No. DE 10 2013 201 554.2 filed Jan. 30, 2013, the disclosure of which is hereby incorporated by reference herein in its entirety.

The invention relates to a device for stabilising a flying attitude of a remote-controlled fixed-wing aircraft. The invention also relates to a method for adjusting parameters with such a device.

In accordance with the prior art, remote-controlled model aircraft are known in general. In order to control such model aircraft, control signals are transmitted by means of a transmitter actuated by the pilot on the ground to a receiver accommodated in the model aircraft. In accordance with the control signals, actuating movements, for example for adjusting control surfaces, motor speed or the like with which the aircraft model can be controlled, are generated by means of actuating devices or servos.

In the case of model aircraft, a distinction is made between helicopters and fixed-wing aircraft. Fixed-wing aircraft are controlled substantially by the movement of control surfaces, for example elevators, rudders, and/or ailerons.

Provided the pilot does not transmit any control signals to the fixed-wing aircraft, this aircraft should maintain its flying attitude in an unchanged manner. In practice, such a desired or predefined flying attitude is changed however by air movements, for example gusts of wind or the like. This is often not identifiable for the pilot due to the distance of the fixed-wing aircraft. It may lead to inaccurate control, which, in flying competitions, may lead to a deduction of points and in the worst case scenario may even lead to a crashing of the fixed-wing aircraft.

DE 199 13 651 B4 discloses a yaw-control system for a remote-controlled helicopter. The yaw-control system comprises a yaw-axis angular velocity sensor and also a mixing unit for mixing a main rotor pitch angle control signal with a yaw-axis control signal. Depending on the values measured by the yaw-axis angular velocity sensor, counter control signals for controlling the tail rotor are generated such that an undesired yawing of the helicopter about the rotor axis is avoided. In this case, a gyroscope system is used as a yaw-axis angular velocity sensor.

DE 199 14 445 B4 describes a control device for a remote-controlled helicopter, with which a misalignment or offset can be suppressed if the control mode is switched over from a proportional control mode to a PID control mode.

DE 10 2005 006 993 B4 discloses an apparatus for the remote control of unmanned missiles. Here, a device for establishing a current flying attitude of the missile is omitted. To avoid manual counter control signals, the control signal is subject to high-pass filtering. In order to form an actuation value, the further signal subjected to high-pass filtering is added at least in part to the original control signal.

EP 2 012 212 A2 discloses a method for the remote control of a model aircraft with use of a gyroscope provided in the model aircraft. In order to improve the control reliability, a second gyroscope is provided. The control signals are influenced with use of the measurement signals generated by the gyroscope and the further gyroscope.

In the case of the control devices known from the field of model helicopters, it is necessary to adjust the sensitivity of the control device. To this end, a parameter influencing the sensitivity of the control is changed until the desired compensation effect specific for the model aircraft is achieved by means of the control device. In order to adjust the parameter, the model aircraft is launched and landed repeatedly, wherein the parameter is changed after each landing. This method is time-consuming and is not particularly accurate.

The object of the invention is to overcome the disadvantages according to the prior art. In particular, a method that can be carried out as easily and as quickly as possible for adjusting parameters in a device for stabilising a flying attitude of a remote-controlled fixed-wing aircraft will be specified. Furthermore, a device with which parameters for stabilising a flying attitude of a remote-controlled fixed-wing aircraft can be adjusted quickly, accurately and easily will be specified.

In accordance with the invention, a method for adjusting parameters in a device for stabilising a flying attitude of a remote-controlled fixed-wing aircraft is proposed, said method comprising the following steps:
providing a remote control comprising a transmitter and a receiver accommodated in the fixed-wing aircraft for receiving control signals transmitted from the transmitter, wherein the receiver is connected to control devices for controlling the fixed-wing aircraft and can be connected selectively to a stabilising device, and wherein the stabilising device can be operated selectively in a stabilising operating mode and in a parameter adjustment operating mode,
wherein, in order to adjust the parameters for at least two axes, the following steps are carried out:
switching on the parameter adjustment operating mode at the stabilising device,
connecting the stabilising device to the receiver during the flight by means of a switch-on signal transmitted from the transmitter,
adjusting a first parameter for a first axis by means of a first adjustment signal transmitted from the transmitter to the stabilising device,
storing the first parameter during the flight as a result of a first memory signal transmitted from the transmitter,
adjusting a second parameter for a second axis by means of a second adjustment signal transmitted from the transmitter to the stabilising device, and
storing the second parameter during the flight as a result of a second memory signal transmitted from the transmitter.

Within the meaning of the present invention, a "fixed-wing aircraft" has a fuselage with wings extending therefrom and also a tail unit. To control a remote-controlled fixed-wing aircraft, at least the control surfaces of the tail unit, that is to say the elevator and the rudder, can be controlled separately from one another by means of the remote control. In the case of a V-tail, the two control surfaces of the V-tail can likewise be controlled suitably such that a movement of the aircraft about a first axis, specifically a pitch axis running through the wings, and also about a second axis, specifically a yaw axis arranged perpendicular to the pitch axis, is therefore possible. Normally, a remote-controlled fixed-wing aircraft also comprises ailerons, with which a movement about a third axis, specifically a roll axis extending in the direction of the fuselage, is possible.

In accordance with the method according to the invention, a parameter operating mode is initially switched on at the stabilising device. This can be implemented for example by actuating a button or switch provided on the stabilising device. For example, a corresponding menu point can therefore be selected and activated on a screen provided on a stabilising device. It is also conceivable however for the parameter adjustment operating mode to be switched on during the flight by a corresponding switching signal transmitted from the transmitter.

The stabilising device is then connected to the receiver during the flight by means of a switch-on signal transmitted from the transmitter. Within the meaning of the present invention, the term "connect" is understood to mean the production of an electrical connection for data and/or signal exchange. When the stabilising device is connected to the receiver, the control signals received by the receiver can be changed by means of the stabilising device. It is also possible for further control signals, for example for generating counter control movements, to be generated by means of the stabilising device.

In the parameter adjustment operating mode, a first parameter for the first axis can now be adjusted by means of a first adjustment signal transmitted from the transmitter to the stabilising device. To this end, a first adjustment signal can be generated at the transmitter by means of a proportional adjustment device. For example, the pilot can change the first adjustment signal by means of a control knob until the fixed-wing aircraft starts to rock or wobble during flight. The first adjustment signal is then reduced such that the fixed-wing aircraft again flies with stable flying attitude, that is to say does not yet start to rock or wobble.

The first parameter can now be stored during the flight as a result of a first memory signal transmitted from the transmitter. A second parameter for the second axis can then be adjusted by means of a second adjustment signal transmitted from the transmitter to the stabilising device, advantageously without the need for an intermediate landing. The second parameter can be adjusted similarly to the adjustment of the first parameter with use of the proportional adjustment device, for example the control knob. Once the second parameter has been adjusted, the second parameter can again be stored, likewise during the flight, as a result of a second memory signal transmitted from the transmitter.

With the proposed method, it is possible to adjust the parameters of the stabilising device quickly and easily during flight. Time-consuming and risky take-off and landing manoeuvres are not necessary for this purpose.

In accordance with an advantageous embodiment, the first and the second parameters are each stored by transmitting a switch-off signal separating the connection between the stabilising device and the receiver. In other words, the switch-off signal can be used as a memory signal. It is thus possible to dispense with the provision of a special radio channel for transmission of the memory signal. The equipment cost for carrying out the method according to the invention can therefore be kept low.

In accordance with a further embodiment of the invention, a maximum control variable relating to a counter control movement, generated by means of the stabilising device, relative to respective axes is adjusted by means of the parameters. In other words, the sensitivity of the counter control can be adjusted with the respective parameter.

The first and/or the second adjustment signal is/are advantageously generated with use of a proportional adjustment device provided at the transmitter. This may be a rotary knob or slider. The provision of a proportional adjustment device enables simple adjustment of the respective parameter.

In accordance with a further particularly advantageous embodiment of the invention, in the parameter adjustment operating mode relating to the second axis, an alternative second parameter can be adjusted by means of alternative second adjustment signals transmitted from the transmitter to the stabilising device and can be stored during the flight as a result of a further memory signal transmitted from the transmitter. The proposed possibility of storing two alternative second parameters for the second axis about which the fixed-wing aircraft is movable by moving the rudder makes it possible to operate the stabilising device in two alternative stabilising operating modes. In a first stabilising operating mode a "heading component" of the rudder can be switched off, and in a second stabilising operating mode a "heading component" of the rudder can be switched on. The second stabilising operating mode is normally required only for specific flying manoeuvres, such as slow rolling or knife-edge flying. Apart from that, the heading component has a rather disadvantageous effect on flying movements of the fixed-wing aircraft because the tail of the fixed-wing aircraft then hangs downwardly in spiraling flight.

In accordance with a further advantageous embodiment, the stabilising device is switched to an alternative parameter adjustment operating mode before the adjustment of the alternative second parameter by means of a further switch-on signal transmitted from the transmitter. In accordance with the proposed embodiment, the pilot has to transmit a further adjustment signal to the stabilising device before the adjustment of the alternative second parameter. This signals to the pilot that he now has to fly into the "heading component" of the fixed-wing aircraft. This further increases the comfort and reliability when adjusting the parameters.

Once at least the first and the second parameter have been adjusted and stored, the parameter adjustment operating mode is switched off at the stabilising device. The parameter adjustment operating mode can be switched off manually at the stabilising device once the fixed-wing aircraft has landed. The adjusted parameters are stored as the parameter adjustment operating mode is switched off. It is possible to change the adjusted parameters after repeated switch-on of the parameter adjustment operating mode.

In accordance with a further advantageous embodiment of the invention, a speed of the fixed-wing aircraft is measured in the stabilising operating mode during the current flight movement, and the maximum control variable predefined by the parameter is increased or reduced in accordance with the measured speed. With the increase in speed, the fixed-wing aircraft responds increasingly sensitively to counter control movements generated by means of the stabilising device. In order to counteract this, the maximum control variable predefined by the parameter can be increasingly reduced, for example with increasing speed.

The speed is expediently measured with use of a GPS sensor or a pitot tube connected to the stabilising device.

In accordance with a further stipulation of the invention, a stabilising device for stabilising a flying attitude of a remote-controlled fixed-wing aircraft is proposed, comprising
a control device and a multi-axis gyro sensor connected thereto, wherein the control device comprises an algorithm for generating stabilising control signals for adjusting actuating devices for controlling the fixed-wing aircraft,
wherein the control device has a first switching device for selective operation in a stabilising operating mode and in a parameter adjustment operating mode,
wherein, in the parameter adjustment operating mode, a separate parameter adjustment mode for each axis of the gyro sensor is provided, in which a parameter corresponding to the respective axis can be adjusted in accordance with an adjustment signal transmitted via a first radio channel, and
wherein the control device comprises a second switching device, with which, upon receipt of a switching signal transmitted via a second radio channel, an adjustment mode can be switched over from a first parameter adjustment mode for a first axis to a second parameter adjustment mode for a second axis.

In the case of the proposed control device, this is basically a micro process computer, with which stabilising control signals are generated in accordance with a predefined algorithm or program. With the stabilising control signals, counter control movements are generated, for example by means of the actuating devices, in the event of a deviation from the predefined flying attitude and are used in order to bring the fixed-wing aircraft back into the predefined flying attitude.

The control device is connected to a multi-axis gyro sensor. This may be a MEMS sensor for example. The signals delivered thereby are evaluated with the algorithm provided in the control device. Suitable stabilising control signals are calculated and generated. The first switching device may be a manual switching device, by means of which the control device can be selectively transferred into the stabilising operating mode or into the parameter adjustment operating mode.

In accordance with an essential aspect of the invention, the stabilising device can be operated in a parameter adjustment operating mode. The control device further comprises a second switching device, by means of which it is possible in the parameter adjustment operating mode to switch further from a first parameter adjustment mode for a first axis to a second parameter adjustment mode for a second axis. Of course, it is also possible by means of the second switching device to switch further to a third parameter adjustment mode for a third axis should the fixed-wing aircraft be designed for control about three axes. By means of the proposed stabilising device, it is thus possible to perform in succession the adjustments of the parameters necessary for the respective fixed-wing aircraft during the flight. It is not necessary to land the fixed-wing aircraft for this purpose. All parameters can be adjusted during a single flying process. The second switching device is implemented in the program for operating the control device. It enables a "switching ahead" from one parameter adjustment mode to the next parameter adjustment mode.

In accordance with an advantageous embodiment of the invention, it is possible by means of the second switching device, upon receipt of a further switching signal transmitted via a second radio channel, to switch over from the second parameter adjustment mode to an alternative second parameter adjustment mode in order to adjust an alternative second parameter. The second parameter may be the parameter for adjusting the rudder in the "normal mode". The alternative second parameter may be an alternative parameter for adjusting the rudder in the "heading mode".

In the "normal mode", counter control movements for compensating a deviation from the flying attitude are generated by means of the control device. The movements of the control devices necessary for this purpose are controlled in this case by means of the algorithm. In the "heading mode", control and counter control movements are generated by means of the stabilising device until the predefined flying attitude has been reached again. In this case, the movements of the control devices are controlled by means of the algorithm, wherein the predefined flying attitude flown before the deviation of the fixed-wing aircraft is used as a control variable. During the control process, the predefined flight attitude is compared constantly to a current flying attitude established by means of the gyro sensor. Control and counter control movements are thus generated until the predefined flying attitude has been reached again.

In accordance with a further embodiment, a speed of the fixed-wing aircraft is measured in the stabilising operating mode during the current flight movement, and a maximum control variable set by the parameter is increased or reduced in accordance with the measured speed. With increasing speed, the maximum control variable by means of which the control devices carry out, for example, a counter control movement is reduced. With increasing speed, small counter control movements are sufficient in order to bring the fixed-wing aircraft back into the predefined flying attitude.

The speed is advantageously measured with use of a GPS sensor or a pitot tube connected to the stabilising device. In particular, GPS sensors are available at reasonable cost. The speed of the fixed-wing aircraft can therefore be measured and transmitted to the control device at relatively low cost. A GPS sensor can be assembled easily in a remote-controlled fixed-wing aircraft. In particular, it does not interfere with the external appearance of the fixed-wing aircraft.

The control device expediently comprises a memory, in which, upon receipt of the switching signal or the further switching signal, the previously adjusted parameter is stored. The control device can be equipped as a process computer control with a memory.

In accordance with a further expedient embodiment of the invention, the stabilising device has a first interface for connection of a speed sensor, preferably a GPS sensor. Furthermore, two second interfaces for connection of control devices can be provided. Three to five second interfaces are expediently provided. Furthermore, at least one third interface for connection of a receiver can be provided. The third interface may a series interface. Two series interfaces can also be provided. Furthermore, three interfaces for DSM2 or DSMX satellite receivers can additionally be provided.

Figure 2:
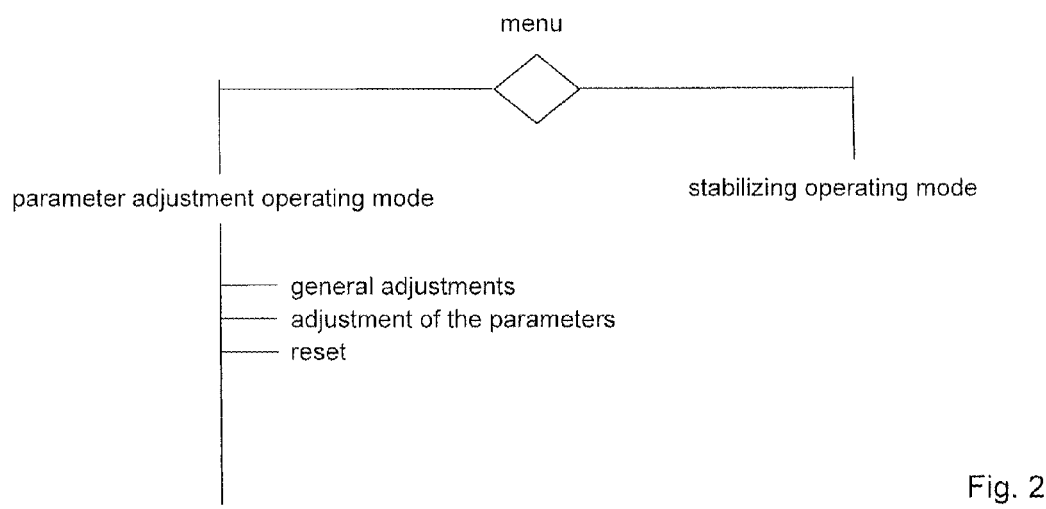
Figure 3:
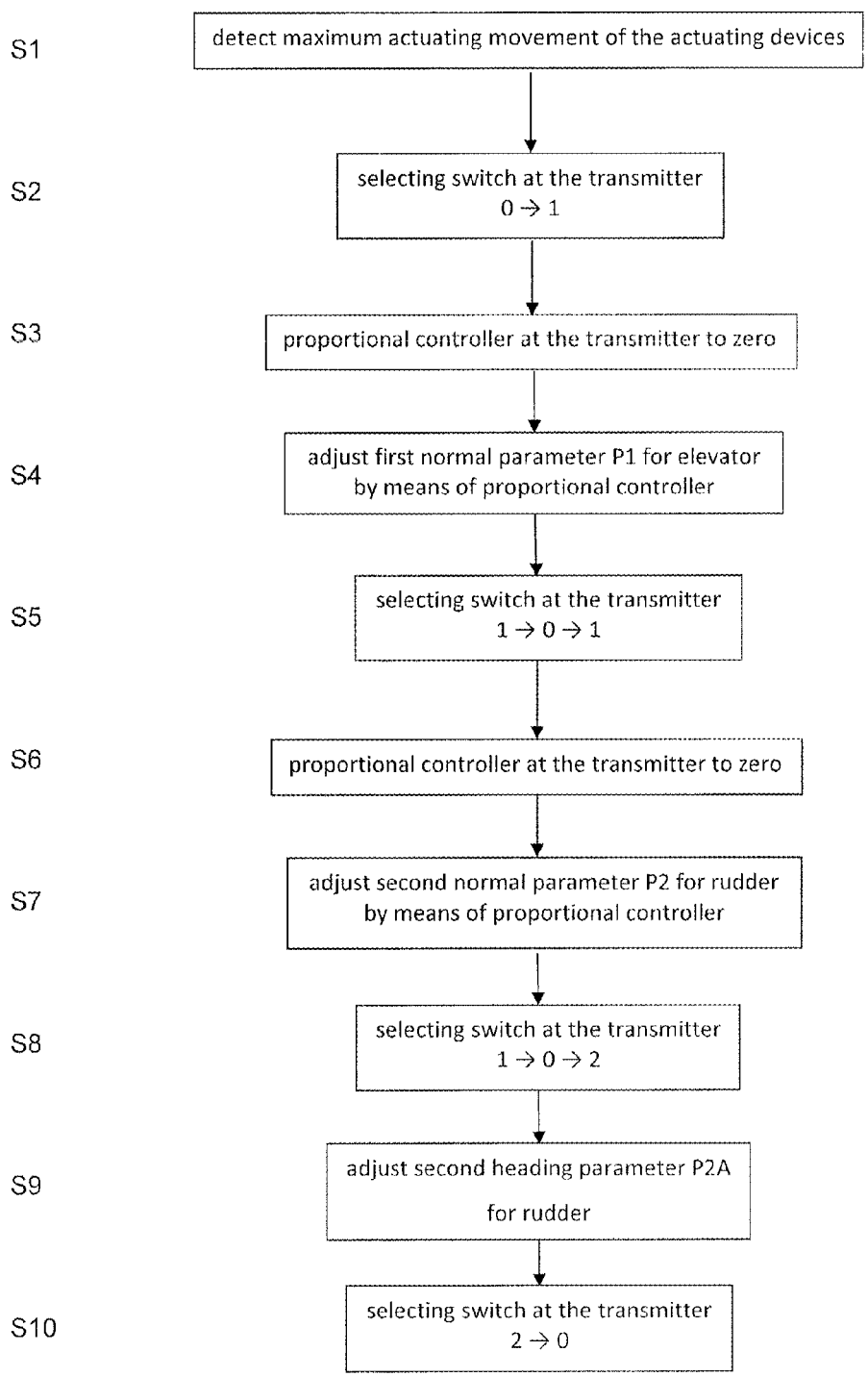

Exemplary embodiments of the invention will be explained in greater detail hereinafter on the basis of the drawings, in which:

FIG. 1 shows a schematic diagram,
FIG. 2 shows a menu structure and
FIG. 3 shows a flow diagram.

FIG. 1 shows a schematic diagram for connecting control components for controlling a remote-controlled fixed-wing aircraft. To receive control signals transmitted from the transmitter 1, a first receiver 2 and also a second receiver 3 are provided here. Reference sign 4 denotes a stabilising device, and reference sign 5 denotes a power supply device. A GPS sensor 6 is connected to a first interface 7 of the stabilising device 4. Five first control devices 8 or servos are connected to second interfaces 9 of the stabilising device 4. The first receiver 2 and the second receiver 3 are connected to two third interfaces 10 of the stabilising device 4. Reference sign 11 denotes second control devices or servos, which are connected to the second receiver 3. The power supply device 5 is connected to the first receiver 2.

The stabilising device 4 comprises a triple-axis gyro sensor (not shown here), for example a MEMS sensor, which can be integrated in a chip with a preamplifier (not shown here). The stabilising device 4 further comprises a screen 12, for example a graphic OLED display, on which a menu for adjusting the stabilising device 4 can be displayed.

The remote-control apparatus shown in FIG. 1 functions as follows.

A control signal transmitted from the transmitter 1 is received for example by the first receiver 2. By means of the first receiver 2, an actuating signal proportional to the control signal is generated and is specific for one of the first actuating devices 8. The first actuating device 8 in question is moved in accordance with the magnitude of the actuating signal. This actuating movement of the corresponding first actuating device 8 can be transmitted, for example via a Bowden cable, to a control surface of the fixed-wing aircraft. As a result of the control surface movement generated by the actuating movement of the first actuating device 8, the fixed-wing aircraft adopts a specific flying attitude. Should the moved control surface be the elevator, the fixed-wing aircraft transitions from horizontal flight into climb flight for example. The climb flight is now detected by the stabilising device 4 as the flying attitude predefined by the actuating signal. Should the fixed-wing aircraft now deviate from the predefined flying attitude as a result of a gust of wind, this is detected with the gyro sensor. As a result, a counter control movement of the elevator is generated in a "normal mode" by means of the stabilising device 4 in accordance with a predefined algorithm. The counter control movement is dimensioned such that the fixed-wing aircraft reverts substantially to the predefined flying attitude. The counter control movement is generated automatically by means of the stabilising device 4 and superimposes the actuating movement caused by the magnitude of the actuating signal. In other words, once the counter control movement has been carried out, the first actuating device 8 readopts the position predefined by the actuating signal.

By means of a selecting switch 13 provided on the transmitter 1, the stabilising device 4 can be transferred from a switched-off state into a "normal mode" and also into a "heading mode" superimposing the "normal mode". In the "heading mode", a flying attitude of the fixed-wing aircraft predefined by the control signal is detected by means of the stabilising device 4 and is buffered as a control variable. In the case of a deviation from the predefined flying attitude, the first actuating device 8 is now moved in the "heading mode" by means of the stabilising device 4 until the buffered predefined flying attitude has been reached again. To this end, a current flying attitude is established constantly by means of the gyro sensor. Control and counter control movements are generated in order to revert to the predefined flying attitude.

The transmitter 1 further comprises a proportional controller denoted by reference sign 14. The proportional controller 14 is used for the adjustment of parameters at the stabilising device 4. Such an adjustment of parameters is necessary in order to adapt the sensitivity of the control and counter control movements effected by the stabilising device 4 to the conditions of the respective fixed-wing aircraft, for example the size and geometry thereof, etc.

A method for adjusting the parameters of the stabilising device 4 is explained in greater detail in FIGS. 2 and 3.

An actuating device with three buttons for navigation in a menu can be connected to the stabilising device 4. In the menu, a parameter adjustment operating mode can be selected, for example. In the parameter adjustment operating mode, basic adjustments can be performed in a menu sub-heading "General Adjustments". For example, these may concern a geometry of the fixed-wing aircraft, a channel association to switches or control sticks, and the like. If the menu sub-heading "Adjustment of Parameters" is selected, parameters can be adjusted with which the sensitivity of the stabilising device 4 with respect to the generation of control or counter control movements is adjusted.

With reference to FIG. 3, a maximum actuating movement of the actuating devices is detected in the menu sub-heading "Adjustment of the Parameters" in a first method step S1. For this purpose, the actuating devices are each transferred maximally in both actuating directions by corresponding movements of the control sticks at the transmitter 1. In a second method step S2, the selecting switch 13 at the transmitter is then placed from position "0" into position "1". The proportional controller 14 provided at the transmitter 1 is then placed to "0" in a third method step S3. The fixed-wing aircraft then takes off and is brought into a horizontal flying attitude. A first normal parameter P1, for example for the elevator, is then adjusted by means of the proportional controller 14. For this purpose, the first normal parameter P1 is increased by means of the proportional controller 14 until the fixed-wing aircraft starts to rock about the elevator axis. The adjustment of the proportional controller 14 is then withdrawn slightly. In a fifth method step S5, the adjusted first normal parameter P1 for the elevator is stored by switching back the selecting switch 13 from the position "1" into the position "0". The selecting switch 13 is then placed back into position "1" in order to adjust a second normal parameter P2 and, in a sixth method step S6, the proportional controller 14 at the transmitter 1 is placed to "0".

In a seventh method step S7, the second normal parameter P2 for the rudder is now adjusted by means of the proportional controller 14. The adjustment occurs similarly to the adjustment of the first normal parameter P1 for the elevator. As soon as the second normal parameter P2 has been adjusted for the rudder, the selecting switch 13 at the transmitter 1 is again brought from the position "1" into the position "0" in an eighth method step S8, whereby the adjusted second normal parameter P2 is stored.

In the eighth method step S8, the selecting switch 13 can now be placed from the switch position "0" to a switch position "2", which enables an adjustment of an alternative parameter for the rudder. This is a second heading parameter P2A. In the case of the rudder, it is expedient to adjust the second heading parameter P2A separately. The adjustment again occurs similarly to the preceding adjustments. The second heading parameter P2A is stored in a tenth method step S10 by moving the selecting switch 13 at the transmitter 1 from the position "2" into the position "0".

The fixed-wing aircraft is then landed and the "parameter adjustment operating mode" is deactivated.

In the case of the method shown in FIG. 3, the adjustment of the normal parameters is described merely for two axes. Of course, it is also possible to adjust normal parameters for a fixed-wing aircraft that can be controlled about three axes, that is to say that has ailerons. Furthermore, the separate adjustment of the heading parameter merely for the rudder is shown in FIG. 3. The heading parameter, in the case of the elevator and the aileron, is advantageously automatically adjusted at the same time as the respective normal parameter. However, as is shown in FIG. 3 for the rudder, it may also be adjusted separately. To this end, similarly to the adjustment of the heading parameter for the rudder, the selecting switch 13 is placed after the adjustment of the normal parameter under the switch position "0" into the switch position "2", and the respective heading parameter is adjusted by means of the proportional controller 14 and is stored.

The proposed method for adjusting parameters with the stabilising device 4 can be carried out easily during a single flight. No intermediate landings or the like are necessary.

LIST OF REFERENCE SIGNS

1 transmitter
2 first receiver
3 second receiver
4 stabilising device
5 power supply device
6 GPS sensor
7 first interface
8 first actuating device
9 second interface
10 third interface 11 second actuating device
12 screen
13 selecting switch
14 proportional controller
P1 first parameter
P2 second parameter
P2A alternative second parameter

The invention claimed is:

1. A method for adjusting parameters in a stabilising device for stabilising a flying attitude of a remote-controlled fixed-wing aircraft, said method comprising following steps of:
   providing a remote control comprising a transmitter and a receiver accommodated in the fixed-wing aircraft for receiving control signals transmitted from the transmitter, wherein the receiver is connected to actuating devices for controlling the fixed-wing aircraft and can be connected selectively to a stabilising device, the actuating devices and the stabilising device being accommodated in the fixed-wing aircraft; wherein the stabilising device can be operated selectively in a stabilising operating mode and in a parameter adjustment operating mode, and wherein the stabilizing device comprises a control device and a multi-axis gyro sensor connected thereto, wherein the control device generates, in the stabilising operating mode, by use of an algorithm, stabilising control signals for adjusting the actuating devices for controlling the fixed-wing aircraft so as to automatically generate counter control movements in an event of a deviation from the predefined flying attitude,
   wherein, to adjust parameters for at least two axes, following steps are carried out:
      switching on the parameter adjustment operating mode at the stabilising device,
      connecting the stabilising device to the receiver during a flight by means of a switch-on signal transmitted from the transmitter,
      adjusting a first parameter for a first axis by means of a first adjustment signal transmitted from the transmitter to the stabilising device,
      storing the first parameter during the flight as a result of a first memory signal transmitted from the transmitter,
      adjusting a second parameter for a second axis by means of a second adjustment signal transmitted from the transmitter to the stabilising device, and
      storing the second parameter during the flight as a result of a second memory signal transmitted from the transmitter.

2. The method according to claim 1, wherein the first parameter and the second parameter are each stored by transmitting a switch-off signal separating connection between the stabilising device and the receiver.

3. The method according to claim 1, wherein a maximum control variable relating to a counter control movement, generated by means of the stabilising device, relative to the respective axes is adjusted by means of the parameters.

4. The method according to claim 3, wherein, in the stabilising operating mode during a current flight movement, a speed of the fixed-wing aircraft is measured, and the maximum control variable predefined by the parameters is increased or reduced in accordance with a measured speed.

5. The method according to claim 4, wherein the speed is measured with use of a GPS sensor or a pitot tube connected to the stabilising device.

6. The method according to claim 1, wherein the first and/or the second adjustment signal is/are generated with use of a proportional adjustment device provided at the transmitter.

7. The method according to claim 1, wherein, in the parameter adjustment operating mode relating to the second axis, an alternative second parameter is adjusted by means of an alternative second adjustment signal transmitted from the transmitter to the stabilising device and can be stored during the flight as a result of a further second memory signal transmitted from the transmitter.

8. The method according to claim 7, wherein, before the adjustment of the alternative second parameter by means of a further switch-on signal transmitted from the transmitter, the stabilising device is switched to an alternative parameter adjustment operating mode.

9. The method according to claim 1, wherein, after the adjustment and storing of at least the first parameter and second parameter, the parameter adjustment operating mode is switched off at the stabilising device.

10. A method for adjusting parameters with a stabilising device for stabilising a flying attitude of a remote-controlled fixed-wing aircraft, said method comprising following steps of:
   providing a remote control comprising a transmitter and a receiver accommodated in the fixed-wing aircraft for receiving control signals transmitted from the transmitter, wherein the receiver is connected to actuating devices for controlling the fixed-wing aircraft and can be connected selectively to a stabilising device, and wherein the stabilising device can be operated selectively in a stabilising operating mode and in a parameter adjustment operating mode,
   wherein, to adjust parameters for at least two axes, following steps are carried out:
      switching on the parameter adjustment operating mode at the stabilising device,
      connecting the stabilising device to the receiver during a flight by means of a switch-on signal transmitted from the transmitter,
      adjusting a first parameter for a first axis by means of a first adjustment signal transmitted from the transmitter to the stabilising device,
      storing the first parameter during the flight as a result of a first memory signal transmitted from the transmitter,
      adjusting a second parameter for a second axis by means of a second adjustment signal transmitted from the transmitter to the stabilising device, and
      storing the second parameter during the flight as a result of a second memory signal transmitted from the transmitter, and
   wherein the first parameter and the second parameter are each stored by transmitting a switch-off signal separating the connection between the stabilising device and the receiver.

11. A method for adjusting parameters with a stabilising device for stabilising a flying attitude of a remote-controlled fixed-wing aircraft, said method comprising following steps of:
   providing a remote control comprising a transmitter and a receiver accommodated in the fixed-wing aircraft for receiving control signals transmitted from the transmitter, wherein the receiver is connected to actuating devices for controlling the fixed-wing aircraft and can be connected selectively to a stabilising device, and wherein the stabilising device can be operated selectively in a stabilising operating mode and in a parameter adjustment operating mode,
   wherein, to adjust parameters for at least two axes, following steps are carried out:

switching on the parameter adjustment operating mode at the stabilising device, connecting the stabilising device to the receiver during a flight by means of a switch-on signal transmitted from the transmitter, adjusting a first parameter for a first axis by means of a first adjustment signal transmitted from the transmitter to the stabilising device, storing the first parameter during the flight as a result of a first memory signal transmitted from the transmitter, adjusting a second parameter for a second axis by means of a second adjustment signal transmitted from the transmitter to the stabilising device, and storing the second parameter during the flight as a result of a second memory signal transmitted from the transmitter, and wherein, in the parameter adjustment operating mode relating to the second axis, an alternative second parameter is adjusted by means of an alternative second adjustment signal transmitted from the transmitter to the stabilising device and can be stored during the flight as a result of a further second memory signal transmitted from the transmitter.

\* \* \* \* \*